US011298325B2

(12) United States Patent
Laczay

(10) Patent No.: US 11,298,325 B2
(45) Date of Patent: Apr. 12, 2022

(54) PHARMACEUTICAL COMPOSITIONS OF PIMOBENDAN

(71) Applicant: Boehringer Ingelheim Vetmedica GmbH, Ingelheim am Rhein (DE)

(72) Inventor: Péter Laczay, Budapest (HU)

( * ) Notice: Subject to any disclaimer, the term of this patent is extended or adjusted under 35 U.S.C. 154(b) by 0 days.

(21) Appl. No.: 17/097,039

(22) Filed: Nov. 13, 2020

(65) Prior Publication Data

US 2021/0059950 A1  Mar. 4, 2021

Related U.S. Application Data

(62) Division of application No. 16/193,425, filed on Nov. 16, 2018, now Pat. No. 10,874,620, which is a division of application No. 14/558,828, filed on Dec. 3, 2014, now Pat. No. 10,172,804.

(30) Foreign Application Priority Data

Dec. 4, 2013  (HU) .................................. P1300702

(51) Int. Cl.
*A61K 9/20* (2006.01)
*A61K 9/50* (2006.01)
*A61K 31/501* (2006.01)
*A61K 31/341* (2006.01)
*A61K 31/55* (2006.01)
*A61K 9/16* (2006.01)
*A61K 45/06* (2006.01)
*A61K 31/585* (2006.01)
*A61K 31/635* (2006.01)

(52) U.S. Cl.
CPC .......... *A61K 9/5031* (2013.01); *A61K 9/1641* (2013.01); *A61K 9/2081* (2013.01); *A61K 9/5015* (2013.01); *A61K 9/5089* (2013.01); *A61K 31/341* (2013.01); *A61K 31/501* (2013.01); *A61K 31/55* (2013.01); *A61K 31/585* (2013.01); *A61K 31/635* (2013.01); *A61K 45/06* (2013.01); *A61K 2300/00* (2013.01)

(58) Field of Classification Search
None
See application file for complete search history.

(56) References Cited

U.S. PATENT DOCUMENTS

| | | |
|---|---|---|
| 4,361,563 A | 11/1982 | Austel et al. |
| 4,569,837 A | 2/1986 | Suzuki et al. |
| 4,585,790 A | 4/1986 | Padfield et al. |
| 4,704,284 A | 11/1987 | Beatty et al. |
| 4,732,915 A | 3/1988 | Ayer et al. |
| 4,851,226 A | 7/1989 | Julian et al. |
| 4,865,851 A | 9/1989 | James et al. |
| 4,933,182 A | 6/1990 | Higashi et al. |
| 4,973,469 A | 11/1990 | Mulligan et al. |
| 5,024,998 A | 6/1991 | Bodor |
| 5,188,836 A | 2/1993 | Muhammad et al. |
| 5,364,646 A | 11/1994 | Gruber et al. |
| 5,571,533 A | 11/1996 | Santus et al. |
| 6,407,079 B1 | 6/2002 | Muller et al. |
| 8,409,612 B1 | 4/2013 | Ethypharm |
| 8,846,679 B2 | 9/2014 | Folger et al. |
| 2003/0059471 A1 | 3/2003 | Compton et al. |
| 2003/0162835 A1 | 8/2003 | Stanisforth et al. |
| 2003/0165565 A1 | 9/2003 | Mehta |
| 2003/0190343 A1 | 10/2003 | Thombre et al. |
| 2003/0212114 A1 | 11/2003 | Sato |
| 2004/0037869 A1 | 2/2004 | Cleverly et al. |
| 2004/0081691 A1 | 4/2004 | Debregeas et al. |
| 2004/0152664 A1 | 8/2004 | Chang et al. |
| 2004/0157887 A1 | 8/2004 | Whittle et al. |
| 2005/0095293 A1 | 5/2005 | Brauns et al. |
| 2005/0203097 A1 | 9/2005 | Folger et al. |
| 2008/0207629 A1 | 8/2008 | Folger et al. |
| 2009/0220611 A1 | 9/2009 | Dargelas et al. |
| 2010/0166857 A1 | 7/2010 | Yan et al. |
| 2010/0183718 A1 | 7/2010 | Ovaert et al. |
| 2011/0028457 A1 | 2/2011 | Roewer et al. |
| 2011/0189283 A1 | 8/2011 | Derrieu et al. |
| 2011/0318420 A1 | 12/2011 | Hu et al. |
| 2012/0148640 A1 | 6/2012 | Folger et al. |
| 2012/0308662 A1 | 12/2012 | Konishi et al. |
| 2013/0115301 A1 | 5/2013 | Bele et al. |
| 2014/0235648 A1 | 8/2014 | Folger et al. |

(Continued)

FOREIGN PATENT DOCUMENTS

| | | |
|---|---|---|
| AU | 2012101682 A4 | 1/2013 |
| CA | 1102240 A | 6/1981 |
| CA | 1222697 A | 6/1987 |
| CA | 2034569 A1 | 7/1991 |
| CA | 1336498 C | 8/1995 |
| CN | 101316595 A | 12/2008 |
| DE | 3728244 A1 | 3/1989 |
| DE | 4001623 A1 | 7/1991 |
| EP | 0306846 A2 | 3/1989 |
| EP | 0330052 A2 | 8/1989 |
| EP | 0335545 A2 | 10/1989 |
| EP | 0439030 A2 | 7/1991 |

(Continued)

OTHER PUBLICATIONS

"Pharmaceutical Necessities". Remington's Pharmaceutical Sciences, 18th Edition, Mack Publishing Company, Easton, Pennsylvania, Chapter 66, 1990, pp. 1288-1300.

(Continued)

*Primary Examiner* — Jessica Worsham
(74) *Attorney, Agent, or Firm* — Andrew Aldag; John Ezcurra

(57) ABSTRACT

A method for the preparation of a composition includes dispersing particulate pimobendan in a molten carrier matrix to form particles coated with the carrier matrix, where the molten carrier matrix includes one or more pharmaceutically acceptable carriers selected from a polyglycolized glyceride, a polyethylene glycol, and combinations thereof, atomizing the dispersion of coated particles, and cooling and collecting the coated particles from the atomized dispersion.

12 Claims, 3 Drawing Sheets

(56) References Cited

U.S. PATENT DOCUMENTS

| | | | |
|---|---|---|---|
| 2015/0025082 | A1 | 1/2015 | Aven et al. |
| 2015/0148335 | A1 | 5/2015 | Bova et al. |
| 2015/0150820 | A1 | 6/2015 | Laczay |
| 2016/0038420 | A1 | 2/2016 | Brunel et al. |

FOREIGN PATENT DOCUMENTS

| | | | |
|---|---|---|---|
| EP | 0241179 | B1 | 11/1991 |
| EP | 1123703 | B1 | 8/2001 |
| EP | 1247456 | A2 | 10/2002 |
| EP | 1260215 | A1 | 11/2002 |
| EP | 1579862 | A1 | 9/2005 |
| EP | 1903039 | A1 | 3/2008 |
| EP | 1920785 | A1 | 5/2008 |
| EP | 2338493 | A1 | 6/2011 |
| EP | 3034071 | A1 | 6/2016 |
| GB | 1045031 | A | 10/1966 |
| GB | 2228004 | A | 8/1990 |
| JP | 61500788 | A | 4/1986 |
| JP | H029825 | A | 1/1990 |
| JP | H0570612 | A | 3/1992 |
| JP | H0570612 | B2 | 10/1993 |
| JP | H11228302 | A | 8/1999 |
| JP | 2001-276597 | A | 10/2001 |
| JP | 2005526738 | A | 9/2005 |
| JP | 2005281283 | A | 10/2005 |
| JP | 2007191419 | A | 8/2007 |
| JP | 2008504308 | A | 2/2008 |
| JP | 2008-534681 | A | 8/2008 |
| JP | 2009-114148 | A | 5/2009 |
| JP | 2011157390 | A | 8/2011 |
| JP | 2013006798 | A | 1/2013 |
| JP | 2013503113 | A | 1/2013 |
| WO | 8502767 | A1 | 7/1985 |
| WO | 1985002767 | A1 | 7/1985 |
| WO | 1995031963 | A1 | 11/1995 |
| WO | 2000069414 | A2 | 11/2000 |
| WO | 2001035925 | A2 | 5/2001 |
| WO | 2002045693 | A1 | 6/2002 |
| WO | 2003074032 | A1 | 9/2003 |
| WO | 2003075895 | A1 | 9/2003 |
| WO | 2004016252 | A1 | 2/2004 |
| WO | 2004060353 | A1 | 7/2004 |
| WO | 2006000229 | A2 | 1/2006 |
| WO | 2006022562 | A1 | 3/2006 |
| WO | 2007036671 | A2 | 4/2007 |
| WO | 2007038796 | A1 | 4/2007 |
| WO | 2007/092026 | A1 | 8/2007 |
| WO | 2007112274 | A2 | 10/2007 |
| WO | 2008055871 | A1 | 5/2008 |
| WO | 2010010257 | A2 | 1/2010 |
| WO | 2010055119 | A2 | 5/2010 |
| WO | 2011009818 | A1 | 1/2011 |
| WO | 2011042463 | A2 | 4/2011 |
| WO | 2011076738 | A1 | 6/2011 |
| WO | 2011131259 | A1 | 10/2011 |
| WO | 2013024023 | A1 | 2/2013 |
| WO | 2013135852 | A1 | 9/2013 |
| WO | 2013164473 | A1 | 11/2013 |
| WO | 2013170317 | A1 | 11/2013 |

OTHER PUBLICATIONS

"Pimobendan". The Merck Index, An Encyclopedia of Chemicals, Drugs, and Biologicals, 13th Edition, Merck Research Laboratories Division of Merck & Co., Inc., Whitehouse Station, NJ, Index 7515, 2001, p. 1332.
"Vetmedin®—1,25 mg appetizing tablets for dogs Veterinary use". Summary of Product Characteristics, SCS Boehringer Ingelheim Comm. V, Mar. 25, 2009, pp. 1-4.
Ahmed et al., "Pharmaceutical challenges in veterinary product development". Advanced Drug Delivery Reviews, vol. 54, 2002, pp. 871-882.
Beaufrere et al., "Therapeutic Review: Pimobendan." Journal of Exotic Pet Medicine, vol. 18, No. 4, Oct. 2009, pp. 311-313.
Boehringer Ingelheim Vetmedica GmbH, 1st International Canine Valvular Disease Symposium, Paris, Oct. 30-31, 2004, pp. 1-45.
Boehringer Ingelheim Vetmedica, Inc. "Freedom of Information Summary: Original New Animal Drug Application". NADA 141-273, Vetmedin, Pimobendan Chewable Tablets, Apr. 30, 2007, pp. 1-46.
Bourezg et al., "Redispersible lipid nanoparticles of Spironolactone obtained by three drying methods." Colloids and Surfaces A: Physicochemical and Engineering Aspects, vol. 413, 2012, pp. 191-199.
Burlage et al., "Other Pharmaceutical Adjuncts"., Physical and Technical Pharmacy, The Blakiston Division: The McGraw-Hill Book Company, Inc., New York, 1963, pp. 653-662.
Dictionary of Veterinary Drugs and Animal Health Products Marketed in France, 12th Edition, 2003, 3 pages.
Dictionnaire Medicament Veterinaire et des produits Sante Animal commercialises en France, 2003, entry for Vetmedin.
El-Badry et al., "Physicochemical Characterization and Dissolution Properties of Meloxicam-Gelucire 50/13 Binary Systems." Scientia Pharmaceutica, vol. 79, 2011, pp. 375-386.
Fasinu et al., "Diverse approaches for the enhancement of oral drug bioavailability." Biopharmaceutics & Drug Disposition, vol. 32, 2011, pp. 185-209.
Fitton et al., "Pimobendan. A Review of its Pharmacology and Therapeutic Potential in Congestive Heart Failure". Drugs and Aging, vol. 4, No. 5, 1994, pp. 417-441.
Hemati et al., "Fluidized bed coating and granulation: influence of process-related variables and physicochemical properties on the growth kinetics". Powder Technology, vol. 13, 2002, pp. 18-34.
International Search Report and Written Opinion for PCT/EP2014/076073 dated Feb. 19, 2015.
Kitzen et al., "Pimobendan". Cardiovascular Drug Reviews, vol. 6, No. 4, 1989, pp. 265-291.
Lachman et al., "The Theory and Practice of Industrial Pharmacy"., 3rd Edition, Lea & Febiger, Philadelphia, 1986, pp. 58-60.
Lai et al., "Real Time and Noninvasive Monitoring of Dry Powder Blend Homogeneity". AIChE Journal, vol. 47, No. 11, Nov. 2001, pp. 2618-2622.
Lantz et al., "Stability of nizatidine in extemporaneous oral liquid preparations". American Journal of Hospital Pharmacy, vol. 47, No. 12, Dec. 1990, pp. 2716-2719.
Lewis et al., "Near-Infrared Chemical Imaging for Product and Process Understanding". in Process Analytical Technology, Second Edition, John Wiley & Sons, Ltd., United Kingdom, 2010, pp. 272-276.
Lezcano et al., "Complexation of Several Benzimidazole-Type Fungicides with Alpha and Beta-Cyclodextrins". Journal of Agricultural and Food Chemistry, vol. 50, 2002, pp. 108-112.
Lindenberg et al., "Classification of orally administered drugs on the World Health Organization Model list of Essential Medicines according to the biopharmaceutics classification system." European Journal of Pharmaceutics and Biopharmaceutics, vol. 58, 2004, pp. 265-278.
Liu et al., "Pharmacology Preparation Technology." Chemical Industry Press, 2006, pp. 113-114.
Loftsson et al., "Pharmaceutical Applications of Cyclodextrins. 1. Drug Solubilization and Stabilization". Journal of Pharmaceutical Sciences, vol. 85, No. 10, Oct. 1996, pp. 1017-1025.
Lyon et al., "Near-Infrared Spectral Imaging for Quality Assurance of Pharmaceutical Products: Analysis of Tablets to Assess Powder Blend Homogeneity". AAPS PharmSciTech, vol. 3, No. 3, Art. 17, Sep. 2002, pp. 1-15.
Menard et al., "Physico-Chemical Aspects of the Complexation of Some Drugs with Cyclodextrins". Drug Development and Industrial Pharmacy, vol. 16, No. 1, 1990, pp. 91-113.
Nainar et al., "Biopharmaceutical Classification System in In-vitro/In-vivo Correlation: Concept and Development Strategies in Drug Delivery." Tropical Journal of Pharmaceutical Research, vol. 11, No. 2, Apr. 2012, pp. 319-329.
Petit et al., "VETMEDIN® 1.25 mg, VETMEDIN® 5 mg, Chewable tablets, Inodilator (pimobendan) tablet for dogs". Dictionary of

(56) References Cited

OTHER PUBLICATIONS

Veterinary Drugs and Animal Health Products Marketed in France, 16th Edition, Les Editions du Point Vétérinaire, 2011, pp. 1658-1661.

Piel et al., "Development of a parenteral and of an oral formulation of albendazole with cyclodextrins". S.T.P. Pharma Sciences, vol. 9, No. 3, 1999, pp. 257-260.

Proceedings of the 1st International Canine Valvular Disease Symposium, Boehringer-Ingeheim Animal Health, 2004.

Redenti et al., "Drug/Cyclodextrin/Hydroxy Acid Multicomponent Systems. Properties and Pharmaceutical Applications". Journal of Pharmaceutical Sciences, vol. 89, 2000, pp. 1-8.

Rudnic et al., "Oral Solid Dosage Forms". Remington: The Science and Practice of Pharmacy, 20th Edition, Lippincott Williams & Wilkins, Baltimore, Maryland, Chapter 45, 2000, pp. 858-870.

Stuber et al., "The Pharmaceutical and Biological Availability of Commercial Preparations of Furosemide". Arzneimittel-Forschung, vol. 32, No. 6, 1982, pp. 693-697.

Sun et al., "Pimobendan." Chemical Industry Press, 2002, pp. 29-30.

Thiel et al., "Content uniformity of microdose tablets (dosage 1 μg-10 mg) produced by fluid bed granulation of interactive mixtures". Journal of Pharmacy and Pharmacology, vol. 38, 1986, pp. 335-343.

Upadhyay et al., "Formulation of Fast-Release Gastroretentive Solid Dispersion of Glibenclamide with Gelucire 50/13." Tropical Journal of Pharmaceutical Research, vol. 11, No. 3, Jun. 2012, pp. 361-369.

Vasconcelos et al., "Solid dispersions as strategy to improve oral bioavailability of poor water soluble drugs." Drug Discovery Today, vol. 12, Nos. 23/24, Dec. 2007, pp. 1068-1075.

Vromans et al., "Densification properties and compactibility of mixtures of pharmaceutical excipients with and without magnesium stearate." International Journal of Pharmaceutics, vol. 46, 1988, pp. 183-192.

Wikipedia, the Free Encyclopedia, "Pimobendan". [Accessed at: http://en.wikipedia.org/wiki/Pimobenan on Mar. 10, 2014].

PHARMACEUTICAL COMPOSITIONS OF PIMOBENDAN

CROSS REFERENCE TO RELATED APPLICATIONS

This application is a division of U.S. patent application Ser. No. 16/193,425 filed on Nov. 16, 2018, which is a division of U.S. patent application Ser. No. 14/558,828 filed on Dec. 3, 2014, now U.S. Pat. No. 10,172,804, which claims priority to Hungarian Patent Application No. P1300702 filed on Dec. 4, 2013, both which are incorporated herein by reference in their entirety.

FIELD OF THE INVENTION

The invention relates to the field of medicine, in particular to the field of veterinary medicine. The invention relates to improvements in the oral formulations of the phosphodiesterase inhibitor pimobendan used for the treatment of congestive heart failure originating from valvular insufficiency or dilated cardiomyopathy and methods of producing the formulations.

BACKGROUND INFORMATION

Pimobendan (4,5-dihydro-6-(2-(4-methoxyphenyl)-1 H-benzimidazol-5-yl)-5-methyl-3(2H))-pyridazinone) is a benzimidazole-pyridazone derivative which was described in EP 0 008 391 as a substance having cardiotonic, hypotensive and antirombotic activities.

EP 0 439 030 discloses the low solubility of pimobendan in aqueous environment which is still characterized by a highly pH-dependent nature. Depending on the buffer system used, about 100 to 300 mg/liter dissolve at a pH between 1 and 3, but at pH 5 only about 1 mg/liter will dissolve in water. In humans, this phenomenon resulted in strongly fluctuating blood concentrations that levels were often too low. These unsatisfactory absorption characteristics were explained by the high pH-dependency of the solubility of pimobendan in aqueous media and by fluctuating pH conditions in the gastrointestinal tract of the test subjects. According to this patent, the low solubility and high pH dependency of the solubility of pimobendan can be overcome by using an intimate dry admixture of powdered pimobendan and powdered citric acid wherein said admixture is up to about one part by weight of pimobendan per no less than about five parts by weight of citric acid and pharmaceutically active carriers, being filled into capsules or compressed into tablets for oral administration. The strongly fluctuating blood concentrations are said to be prevented by the acid microsphere, which is caused by the dissolving rate of citric acid, formed around the pimobendan particles. Said microsphere is always acidic and ensures a reliable, practically pH-independent dissolution and absorption of pimobendan.

WO 2005/084647 relates to a novel solid formulation comprising pimobendan which is homogeneously dispersed in a polyvalent acid selected from the group consisting of citric acid, acetic acid, maleic acid, tartaric acid or its anhydride, and a flavoring substance. According to said publication, the high quantity of citric acid and the acidic taste of it is not readily accepted by most animals. Thus, these formulations have to be force-fed to the animals or mixed with food prior to application. According to WO 2005/084647, these difficulties can be overcome by using this novel formulation preferably in the form of tablets. Most preferred is a tablet characterized in that the tablet comprises 1.25 mg, 2.5 mg, 5 mg or 10 mg pimobendan, and further comprises citric acid, preferably at an amount of 50 mg/g of the solid formulation, artificial beef flavor and pharmaceutically acceptable excipients.

WO 2010/055119 discloses a novel formulation, comprising pimobendan and an organic carboxylic acid, wherein the only organic carboxylic acid is succinic acid, and the weight ratio of succinic acid to pimobendan is at least 11:1.

WO 2010/010257 relates to the use of a coating composition for application to a solid veterinary pharmaceutical composition made from pimobendan by a method of film coating comprising a powder appetizing material, a binder and a solvent.

EP 2 338 493 provides new crystalline forms of pimobendan, the solubility characteristics of which are such that adding an organic acid or an anhydride thereof is not needed for ensuring a satisfactory resorption of the substance.

As regards to its biopharmaceutics properties, pimobendan can be classified in Class IV in the Biopharmaceutics Classification Systems (BSC). This means that it exhibits challenging molecular properties such as low solubility and low permeability; both of them are considered rate-limiting steps for absorption. However, the unsatisfactory absorption characteristics of pimobendan can be explained primarily by the high pH-dependency of its solubility in aqueous media and by fluctuating pH conditions in the gastrointestinal tracts of the target animals to be treated. It is known that even the pH of the gastric juices may vary in a relatively wide range, namely between 1 and 5, depending on the presence of food. The fasted gastric pH in dogs was found to vary between 0.9 and 2.5, whereas the gastric pH may exhibit a 2-3 pH unit elevation in the first postprandial hour. In addition, the intestinal juices are also characterized by fluctuating pH conditions ranging from 3 to 7.5.

According to the state in the art, the unsatisfactory absorption of pimobendan due to its high pH-dependency of solubility is prevented by simultaneously administering great amounts of an organic acid in the formulation or using a different crystalline form (polymorph) of the sub stance.

The objective underlying the present invention is therefore to provide an improved pimobendan formulation, which overcomes the problems of the prior art.

SUMMARY OF THE INVENTION

Surprisingly, the inventor has now succeeded in overcoming the high pH-dependency of the solubility of pimobendan and ensuring a very satisfactory dissolution rate at all pH conditions representing the gastrointestinal tract and therefore a satisfactory absorption, even if there are considerable pH fluctuations in the gastrointestinal tract, without using an organic carboxylic acid or modifying the crystalline form of the substance by applying the lipid embedding (lipid coating) approach. The lipid-embedded particles of pimobendan are produced by using the spray congealing technology, for example as described in U.S. Pat. No. 4,865,851. Spray congealing (also known as spray chilling) is one of the methods used to produce microparticles or more specifically microspheres. These are solid, approximately spherical particles with sizes in the micrometer range, in which the drug is evenly distributed within the entire volume of the particle. The embedded particles exhibit a rapid and substantial dissolution of pimobendan from oral formulations at each pH representing the gastrointestinal tract of target animals ensuring an adequate absorption of the drug independently from the highly varying pH conditions. The spray congealing technology elaborated for production of the lipid-embedded particles is rapid, easily scaled-up and low expensive. It is environmentally friendly as no solvent is required in the formulation and manufacturing process. Using the lipid-embedded particles it was possible to formulate palatable oral pimobendan formulations which are rapidly and substantially dissolving at all pH conditions representing the milieu(s) of the gastrointestinal tract without including any acidic compounds.

In one aspect, the objective of the present invention has surprisingly been solved by providing a composition comprising pimobendan in particulate form coated with a carrier matrix, wherein the carrier matrix consists essentially of one or more pharmaceutically acceptable carriers selected from the following groups:
  a. polyglycolized glycerides,
  b. polyethylene glycols (PEGs).

In another aspect, the objective of the present invention has surprisingly been solved by providing a composition comprising pimobendan in particulate form coated with a carrier matrix, wherein the carrier matrix consists essentially of one or more pharmaceutically acceptable carriers selected from the following groups:
  a. polyglycolized glycerides,
  b. polyethylene glycols (PEGs),
and wherein the coating with the carrier matrix serves to ensure a rapid and substantial dissolution of pimobendan irrespective of the pH conditions.

In yet another aspect, the objective of the present invention has surprisingly been solved by providing a process for the preparation of a composition as herein disclosed, which comprises
  a. dispersing particulate pimobendan in a molten carrier matrix,
  b. atomizing the dispersion obtained in step (a), and
  c. cooling and collecting the coated particles.

In yet another aspect, the objective of the present invention has surprisingly been solved by providing a composition comprising pimobendan in particulate form coated with a carrier matrix obtainable by the processes for the preparation of a composition as disclosed herein.

In yet another aspect, the objective of the present invention has surprisingly been solved by providing a pharmaceutical composition for oral administration to warm-blooded animals, preferably companion animals, in particular dogs, comprising a veterinarily effective amount of the composition as described herein, one or more physiologically acceptable excipients, and optionally, veterinarily effective amounts of one or more further active ingredients selected from the groups of angiotensin enzyme (ACE) inhibitors, aldosterone antagonists and/or loop diuretics.

By applying the pharmaceutical composition according to the present invention, the low solubility and high pH-dependency of solubility of pimobendan can be overcome without administering simultaneously great amounts of organic acid or using a different crystalline form (polymorph) of the substance as it is demonstrated by the rapid and substantial dissolution of the active compound at each pH representing the milieu(s) of the gastrointestinal tract of animals. The practically pH-independent dissolution ensures satisfactory absorption even at fluctuating pH conditions of the treated subjects.

DETAILED DESCRIPTION OF THE INVENTION

Figure 1:
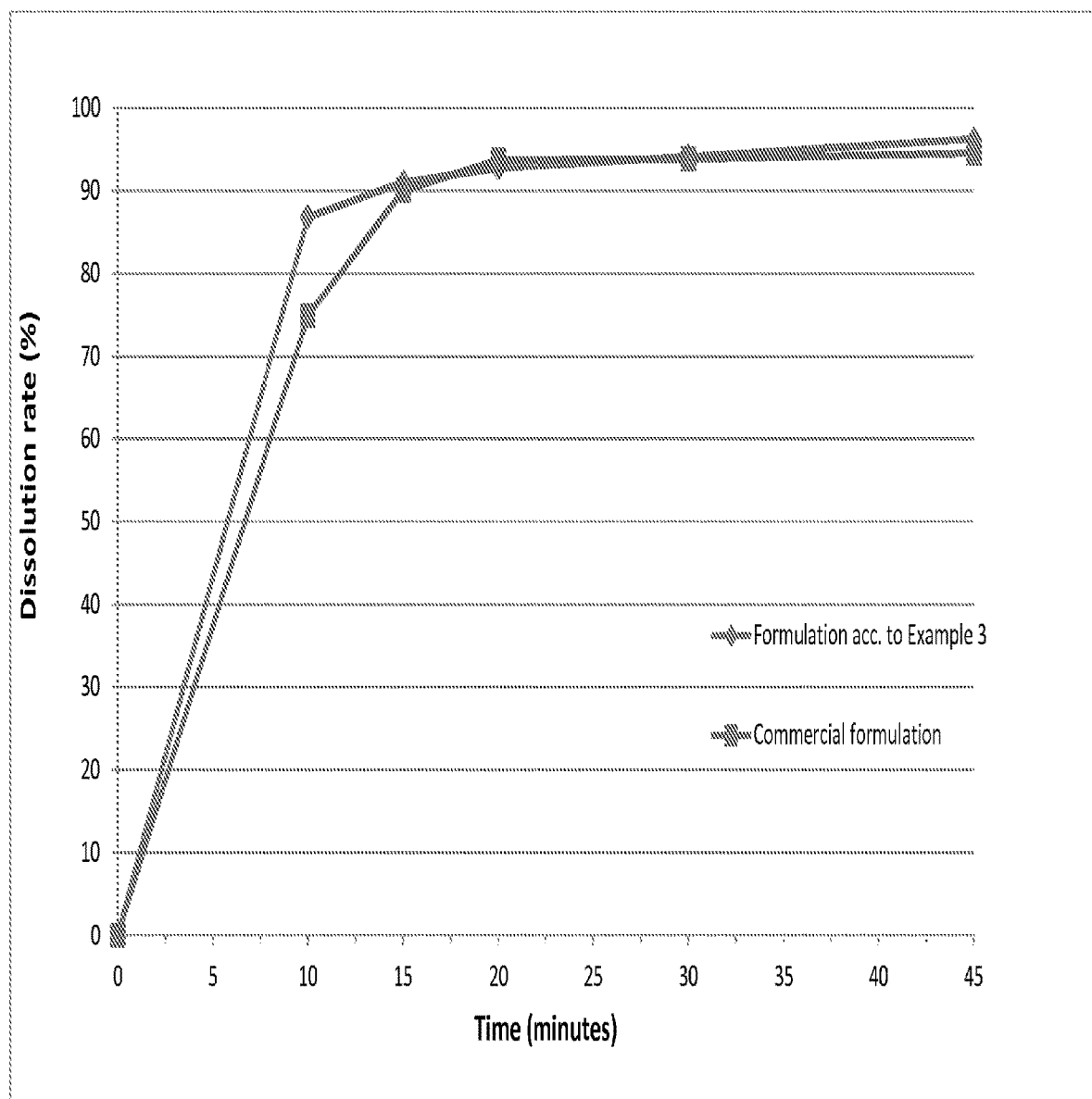
FIG. 1: Comparative dissolution profiles of tablet formulations containing 5 mg pimobendan prepared according to Example 3 of the invention and available commercially as chewing tablets, respectively in highly acidic pH region (pH 1.2). Conditions of testing: V=1000 ml, rotation speed=100 rpm, chromatographic conditions: Agilent Infinity 1290 UHPLC, RP18, 50×3.0 mm, 1.7 µm column, 27:73 v/v % acetonitrile:phosphate buffer as mobile phase, 0.4 ml/min flow rate, 290 nm detection wavelength.

Before the embodiments of the present invention are described in further details it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

In one aspect, the objective of the present invention has surprisingly been solved by providing the process for the preparation of a composition as herein disclosed, which comprises
  a. dispersing particulate pimobendan, preferably with a mean particle size of less than 20 µm, in a molten carrier matrix, such as polyglycolized glycerides, preferably stearoyl macrogol-32 glycerides, more preferably Gelucire 50/13, and/or polyethylene glycols, preferably with an average molecular weight of 1.500 to 20.000 g/mol, more preferably with an average molecular weight of 4.000 to 6.000 g/mol, most preferably PEG 6000, wherein the carrier matrix preferably has a melting point from 40° C. to 80° C., more preferably from 50° C. to 70° C., by using conventional dispersion techniques, for example, using a high shear mixer, to yield a dispersion, preferably a homogenous suspension;
  b. atomizing the dispersion obtained in step (a) by using conventional atomizers, such as rotary atomizers, pressure or pneumatic nozzles and/or sonic nozzles, preferably fitted in a standard spray congealing/chilling apparatus, more preferably by using a two-fluid pressure or pneumatic nozzle atomization system fitted in a standard spray congealing/chilling apparatus, using atomizing gas pressures of 1 to 10 bar, preferably 2 to 8 bar and more preferably 3 to 6 bar; and c. cooling and collecting the coated particles by conventional cooling and collecting techniques, for example, by applying a stream of cool air or an inert gas, such as dry nitrogen, preferably at a temperature of 0° to 30° C., more preferably at a temperature of 3° to 15° C., even more preferably at a temperature of 5° to 15° C., most preferably at a temperature of 4° to 8° C., to the spray apparatus and collecting the particles, preferably in a cyclone separator or a bag filter.

According to a further aspect, the objective of the present invention has surprisingly been solved by providing a composition comprising particles of pimobendan with an integral coating of a carrier matrix, wherein the carrier matrix consists essentially of one or more pharmaceutically acceptable carriers from the groups of polyglycolized glycerides and polyethylene glycols, and wherein the pimobendan exhibits from the composition or relevant drug forms a rapid and extensive (fast and substantial) dissolution at all pH conditions representing the milieu(s) of the gastrointestinal tract of target animals.

According to a further aspect, the present invention provides pharmaceutical compositions for oral administration in companion animals, particularly in dogs, which comprise lipid-embedded particles of pimobendan in suitable vehicle.

According to a yet further aspect, the invention provides a method of ensuring a reliable, rapid and substantial dissolution of pimobendan at each pH condition representing the gastrointestinal tract of target animals which comprises coating of pimobendan with a suitable carrier and incorporating the embedded particles into oral formulations, for example into tablets.

In order to effectively overcome the high pH-dependency of the solubility of pimobendan and provide coated particles exhibiting rapid and substantial dissolution at all pH conditions representing the gastrointestinal tract of dogs, the mean diameter of the coated pimobendan particles should preferably be less than 50 μm.

The melting point of the carrier should be sufficiently high to prevent melting of the coated particles in the mouth, but not so high that pimobendan itself melts and/or becomes chemically degraded during the coating process. Thus, the carrier or a mixture of carriers used as carrier matrix in the present invention will have a melting point from 40° C. to 80° C. and preferably from 50° C. to 70° C.

Suitable carriers for the coating of pimobendan are selected from the groups of polyglycolized glycerides and polyethylene glycols.

Polyglycolized glycerides are mixtures of glycerides of fatty acids and esters of polyoxyethylene with fatty acids. In these mixtures, the fatty acids are saturated or unsaturated and the glycerides are mono-, di- or tri-glycerides or mixtures thereof in any proportions. Examples of suitable polyglycolized glycerides include but are not limited to lauroyl macrogolglycerides or stearoyl macrogolglycerides.

In a particular group of compositions, the polyglycolized glycerides contained in the carrier matrix have a hydrophilic-to-lipophilic balance value (HLB) of greater than 10. In a further particular group of compositions, the polyglycolized glycerides contained in the carrier matrix are dispersible in water. In a further particular group of compositions, the polyglycolized glycerides are stearoyl macrogolglycerides. In yet a further particular group of compositions, the polyglycolized glyceride is stearoyl macrogol-32 glycerides (for example Gelucire 50/13). Stearoyl macrogol-32 glycerides are semi-solid/solid at room temperature, having a melting point of 50° C.

Polyethylene glycols USP (PEGs), alternatively known as macrogels, are hydrophilic polymers of oxyethylene. PEGs having an average molecular weight greater than 900 g/mol are generally semi-solid or solid at ambient temperature. A suitable average molecular weight range for PEGs in the present invention is 1.500 to 20.000 g/mol. Suitable commercially available products include but are not limited to PEG 1500, PEG 4000 and PEG 6000. In a particular group of compositions, the PEG(s) present in the carrier matrix have an average molecular weight range of between 4.000 and 6.000 g/mol. In a further particular group of formulations of this embodiment, this PEG has an average molecular weight of around 6.000 g/mol.

According to one embodiment of the present invention, the carrier matrix used for coating of pimobendan consists of one or more pharmaceutically acceptable carriers selected from the groups of polyglycolized glycerides and polyethylene glycols.

In a further embodiment of the invention, the carrier matrix is a polyglycolized glyceride. Conveniently, the polyglycolized glyceride is lauroyl macrogolglycerides or stearoyl macrogolglycerides, particularly stearoyl macrogol-32 glycerides.

In yet a further embodiment of the invention, the carrier matrix is a polyethylene glycol, particularly PEG 6000.

In a further embodiment of the invention, the carrier matrix comprises a mixture of at least one polyglycolized glyceride and at least one polyethylene glycol. Conveniently, the polyglycolized glyceride present in this embodiment is stearoyl macrogol-32 glycerides and suitably the stearoyl macrogol-32 glycerides is present in an amount to make up 10-100% by weight of the carrier matrix component of the composition, and preferably represents 20-50% by weight of the carrier matrix component of the composition. Conveniently, the polyethylene glycol present in this embodiment has an average molecular weight between 4.000 and 6.000 g/mol and suitably the PEG is present in an amount to make up 10-100% by weight of the carrier matrix component of the composition, and preferably 30-80% by weight of the carrier matrix component of the composition. Preferably, there is only one polyglycolized glyceride and one polyethylene glycol present in this embodiment.

In a particular group of formulations of this embodiment, this polyglycolized glyceride belongs to the stearoyl macrogol-32 glycerides and the PEG has an average molecular weight of 6.000 g/mol. Preferably, the stearoyl macrogol-32 glycerides and the polyethylene glycol 6000 are independently from each other present in amounts to make up 10% by weight to 100% by weight of the carrier matrix component of the composition, preferably 20% by weight to 75% by weight of the carrier matrix component of the composition, more preferably 20% by weight to 50% by weight of the carrier matrix component of the composition.

The lipid-coated particles according to the invention will contain 1 to 80%, preferably 5 to 30%, more preferably 10 to 20% pimobendan on a weight-to-weight (w/w) basis.

The lipid-coated particles of the invention are characterized by a median (D50) value of particle size distribution of generally less than 500 μm, preferably less than 300 μm, more preferably less than 250 μm and even more preferably less than 200 μm. Control of the particle size is necessary to ensure that the dissolution of pimobendan from the subsequently formulated product will be rapid and substantial at all pH conditions representing the gastrointestinal tract of the target animals. Coated particles having a D50 value of less than 200 µm are preferred in this respect. The D50 value represents the median particle size in a given particle size distribution, i.e. the particle size value which 50% of all particles are smaller than. For instance, a D50 value of 200 µm means that 50% of all particles have a particle size smaller than 200 µm.

The lipid-coated particles of the invention may be prepared by atomizing a dispersion of pimobendan in a molten carrier matrix and cooling the particles hereby obtained and such a process constitutes a further feature of the invention. The dispersion may be prepared by adding particulate pimobendan to the molten carrier or mixture of carriers or alternatively mixing the ingredients of the dispersion together in the solid state and melting the carrier matrix. The particulate pimobendan can be dispersed in the molten carrier matrix using conventional techniques, for example, using a high shear mixer. Generally, the temperature of the molten carrier matrix should be 20-40° C. above its melting point. In general, the carrier or mixture of carriers used for coating of pimobendan particles should have a melting point within the range of 40 to 80° C., preferably 50 to 70° C., and the temperature of the molten carrier matrix will be 20 to 40° C. above its melting point. Atomizing techniques which may be applied include the use of conventional atomizers such as rotary atomizers, pressure nozzles and sonic nuzzles. The use of a two-fluid nozzle atomizer fitted in a standard spray congealing/chilling apparatus is particularly convenient.

In the atomization process, the molten dispersion will generally be supplied to the atomizer head at a temperature in the range of 70° C. to 100° C., preferably 75° C. to 95° C., more preferably 75° C. to 90° C., the precise temperature depending on the particular carrier matrix used. The atomizing gas supplied to the nozzle may be air or an inert gas such as nitrogen. The pressure of the atomizing gas is between 1 and 10 bar, preferably between 2 and 8 bar and more preferably between 3 and 6 bar. The atomizing pressure is desirably controlled in order to produce particles of the preferred size.

The coated particles may be solidified and collected by conventional techniques. The coated particles may conveniently be solidified by applying a stream of cool air or dry nitrogen to the spray chamber at a temperature between 0° C. to 30° C., preferably 3° C. to 15° C., more preferably 5° C. to 15° C., most preferably 4° C. to 8° C. The lipid-coated particles are collected as a free flowing powder using either a cyclone separator or a bag filter. The coated particles are spherical in shape and have a D50 value of less than 500 µm, preferably less than 300 µm, more preferably less than 250 µm, and even more preferably less than 200 µm.

The lipid-coated particles of the invention may be incorporated into a pharmaceutical composition for oral administration, using further pharmacologically active ingredients and/or physiologically acceptable carriers and/or excipients.

The compositions according to the invention may for example include tablets, granules, powders, suspensions, oral pastes and gels. Tablets including chewable tablets represent the particularly preferred dosage form.

Accordingly, the present invention relates in one embodiment to an oral pimobendan formulation, preferably a tablet, comprising
    a veterinarily effective amount of pimobendan as active substance in the lipid-coated particulate form, and physiologically acceptable excipients.

The amount of pimobendan in the oral formulations is preferably in the range of 0.01% to 10% by weight, more preferably 0.5% to 1.0% by weight, based on the entire formulation.

The oral pimobendan formulations of the present invention may also comprise veterinarily effective amounts of further active ingredients which may be selected from angiotensin converting enzyme (ACE) inhibitors, aldosterone antagonists and/or loop diuretics. Non-limiting examples of actives which may be used in combination with the lipid-coated pimobendan particles according to the invention are: benazepril (CAS No. 86541-75-5), spironolactone (CAS No. 52-01-7) and/or furosemide (CAS No. 54-31-9), all and independently from each other in free form or in the form of a physiologically acceptable salt, which preferably is embedded into a (lipid) carrier matrix. That is the further active substances may also be added to the oral pimobendan formulations in the form of lipid-embedded particles, produced by using the spray congealing technique, i.e. particles coated with a (lipid) carrier matrix. Preferably, the oral pimobendan formulations of the present invention also comprise veterinarily effective amounts of benazepril, in free form or in the form of a physiologically acceptable salt, which preferably is embedded into a carrier matrix. The further active substances may be present in the oral formulations of the invention in the range of 0.01 to 50% by weight, preferably from 0.1 to 20% by weight, based on the entire weight of the formulation/composition.

The oral pimobendan compositions may be formulated using conventional pharmaceutically acceptable excipients. Thus for example tablets may be prepared by using binding agents (e.g. pregelatinised starch, polyvinyl pyrrolidine or hydroxypropyl methyl cellulose), fillers (e.g. lactose, microcrystalline cellulose or calcium hydrogen phosphate), lubricants (e.g. magnesium stearate, talc or colloidal silica), disintegrants (e.g. starch or sodium starch glycolate) or wetting agents (e.g. sodium lauryl sulphate). The tablet formulations of the present invention, in addition, contain one or more attractive, physiologically acceptable natural or synthetic flavorings. Preferred flavoring agents are artificial beef flavor, liver powder and brewer's yeasts. The flavoring agents are present preferably in the tablet formulations of the invention in the range of 1.0% by weight to 60% by weight, more preferably from 5.0% by weight to 30% by weight, based on the entire weight of the formulation/composition.

The oral paste or gel formulation of the present invention, may contain pharmacologically acceptable excipients, for example thickeners (e.g. xanthan gum, polyvinyl pyrrolidones, polyacrilates such as carbopols, cornstarch, microcrystalline cellulose, hydroxyethyl cellulose, silicon dioxide or combinations thereof), humectants (e.g. glycerol), preservatives (e.g. benzyl alcohol, benzoic acid, benzoates or p-hydroxibenzoates, pH-adjusting agents (bases or acids), binders, fillers, surface active or dispersing agents. Said pharmacologically acceptable excipients are known to those skilled in the art of veterinary formulation technology. The oral paste and gel formulations of the present invention also contain veterinarily acceptable attractive flavorings. Suitable flavoring agents within the compositions of the invention are, for example, artificial beef flavor, food extracts such as desiccated liver or malt extract and honey flavors.

The pharmaceutical compositions of the invention may be prepared according to conventional techniques well known in the pharmaceutical industry. Thus, for example tablets may be prepared by direct compression of a dry admixture of the lipid-coated pimobendan particles with excipients and optionally with further active substances or by wet granulation. Oral paste or gel formulations may be obtained by dispersing the lipid-coated particles of pimobendan and optionally further active ingredients in suitable vehicles.

The compositions for use according to the present invention may, if desired, be presented in a pack or dispenser device which may contain one or more unit doses. The pack may for example comprise metal or plastic foil, such as blister pack.

The formulations of the present invention are suitable for the treatment of congestive heart failure originating from valvular insufficiency or dilated cardiomyopathy in companion animals, in particular in dogs.

The efficacy is based on a satisfactory dissolution and subsequent absorption of the active substance. The dissolution profiles obtained from the tablet formulation according to the present invention and those from commercially available tablets, both of them containing 5 mg pimobendan, were compared at pH 1.2, 4.5 and 7.5 buffers, i.e. at pH conditions representing different parts/milieus of the gastrointestinal tract of companion animals. The dissolved concentrations of pimobendan were determined by a validated UHPLC method.

The oral formulations according to the present invention exhibit a high palatability meaning the voluntary acceptance or ingestion of the formulations by warm-blooded animals, for instance companion animals, in particular by dogs. The acceptance of the oral formulations containing lipid-coated pimobendan particles and suitable further ingredients according to the present invention was tested on dogs.

EXAMPLES

The following examples serve to further illustrate the present invention; but the same should not be construed as a limitation of the scope of the invention disclosed herein.

Example 1—Lipid Coating of Pimobendan

Gelucire 50/13 (18.0 kg) was melted in a stainless steel vessel and raised to a temperature of 85° C. Pimobendan (2.0 kg) with a mean particle size <20 µm was added to the molten lipid. The molten dispersion was mixed with a high shear mixer to give a homogeneous suspension and pumped to a spray congealing apparatus. The mixture was atomized using a two-fluid nozzle atomization system at atomizing gas pressures of 3 to 6 bar. The atomized droplets were chilled using air fed into the spray chamber at a temperature of 5 to 10° C. and the solid particles were collected in a cyclone separator. The lipid-coated pimobendan comprised spherical particles with a mean particle size of 90 µm.

Example 2—Lipid Coating of Pimobendan

Gelucire 50/13 (4.5 kg) and PEG 6000 (13.5 kg) were melted in a stainless steel vessel while raising the temperature to 90° C. To this was added pimobendan (2 kg) with a particle size of <20 µm. The molten dispersion was subjected to high shear mixing to obtain a homogenous suspension and this mixture was spray chilled as described in Example 1, to give a lipid-coated product having a similar particle size and shape. For example, three different batches were produced with D50 values of 118 µm, 136 µm and 166 µm, respectively.

Example 3—Tablet Formulation

Pimobendan embedded into a carrier matrix comprising Gelucire 50/13 and PEG 6000 was blended with pig liver flavor, yeast powder and further excipients in a rotary blender. The resultant mixture was compressed into tablets using a suitable tablet press and suitable punches.

| Direct Compression Tablets | Amount (% w/w) |
| --- | --- |
| Lipid-coated Pimobendan | 6.3 |
| Lactose | 20.5 |
| Pig liver powder | 20.0 |
| Microcrystalline cellulose | 19.0 |
| Pregelatinised starch | 11.2 |
| Sodium starch glycolate | 10.0 |
| Yeast powder | 10.0 |
| Talc | 2.0 |
| Magnesium stearate | 1.0 |

Example 4—Tablet Formulation

Pimobendan coated with Gelucire 50/13, furosemide and the excipients were blended in a rotary mixer, and then the blend was compressed into tablets using a suitable tablet press and suitable punches.

| Oral Tablet | Amount (% w/w) |
| --- | --- |
| Lipid-coated Pimobendan | 3.1 |
| Furosemide | 5.0 |
| Lactose | 25.0 |
| Microcrystalline cellulose | 21.9 |
| Artificial beef flavor | 20.0 |
| Pregelatinised starch | 14.0 |
| Sodium starch glycolate | 8.0 |
| Talc | 2.0 |
| Magnesium stearate | 1.0 |

Example 5—Tablet Formulation

The lipid-embedded particles of pimobendan prepared according to Example 2 were blended with lipid-coated benazepril, the particles of which were embedded into a carrier matrix comprising glycerol distearate, yeast powder, synthetic liver aroma and further excipients, in a rotary blender, and then the resultant mixture was compressed into tablets using a suitable tablet press.

| Direct Compression Tablets | Amount (% w/w) |
| --- | --- |
| Lipid-coated Pimobendan | 6.3 |
| Lipid-coated Benazepril | 12.5 |
| Yeast powder | 25.0 |
| Sodium starch glycolate | 15.0 |
| Microcrystalline cellulose | 13.2 |
| Lactose monohydrate | 12.5 |
| Pregelatinised starch | 10.0 |
| Synthetic liver flavor | 3.5 |
| Talc | 2.0 |

Example 6—In Vitro Dissolution

Figure 2:
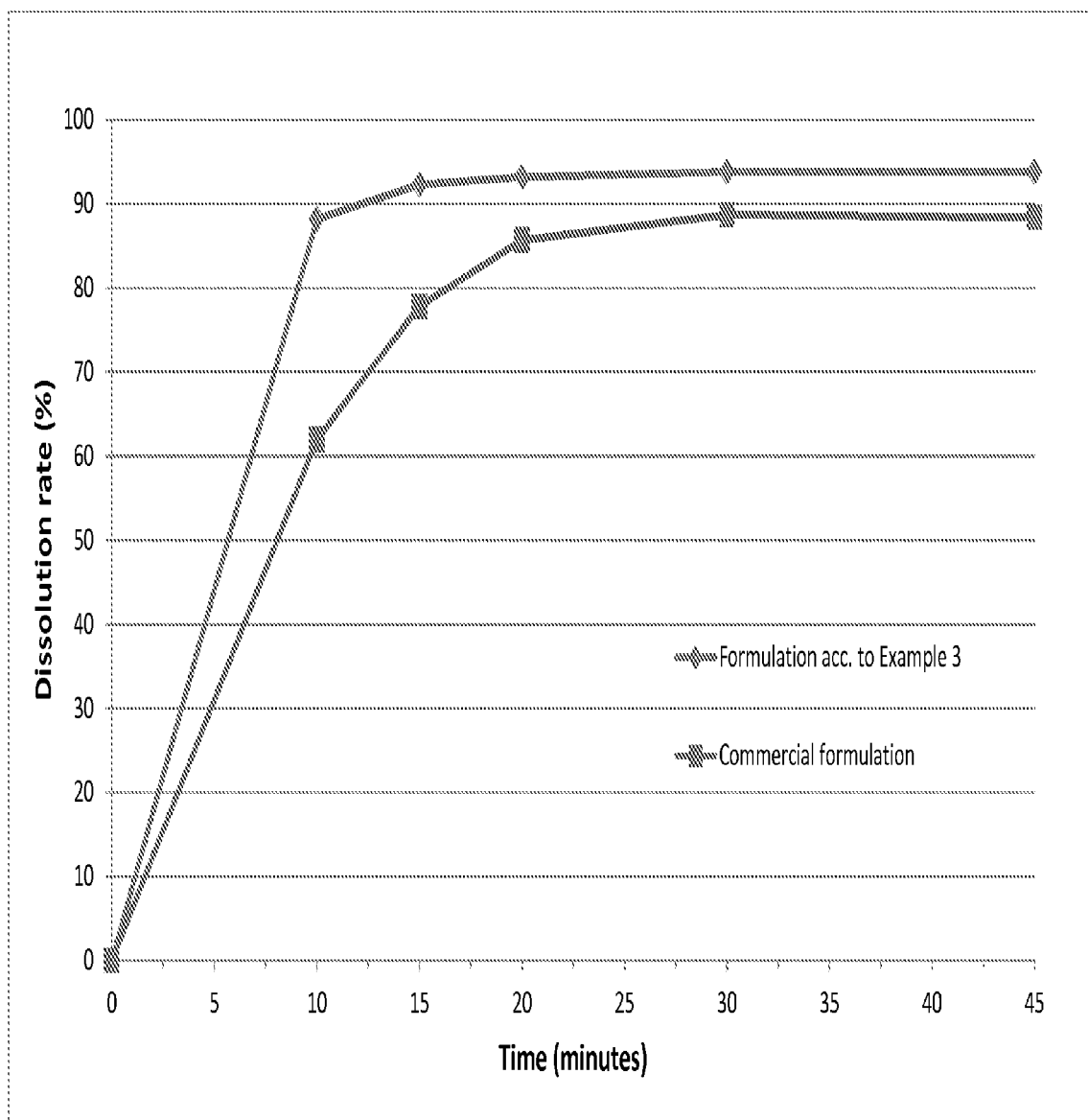
FIG. 2: Comparative dissolution profiles of tablet formulations containing 5 mg pimobendan prepared according to Example 3 of the invention and available commercially as chewing tablets, respectively in moderately acidic pH region (pH 4.5). Conditions of testing are the same as for FIG. 1.
Figure 3:
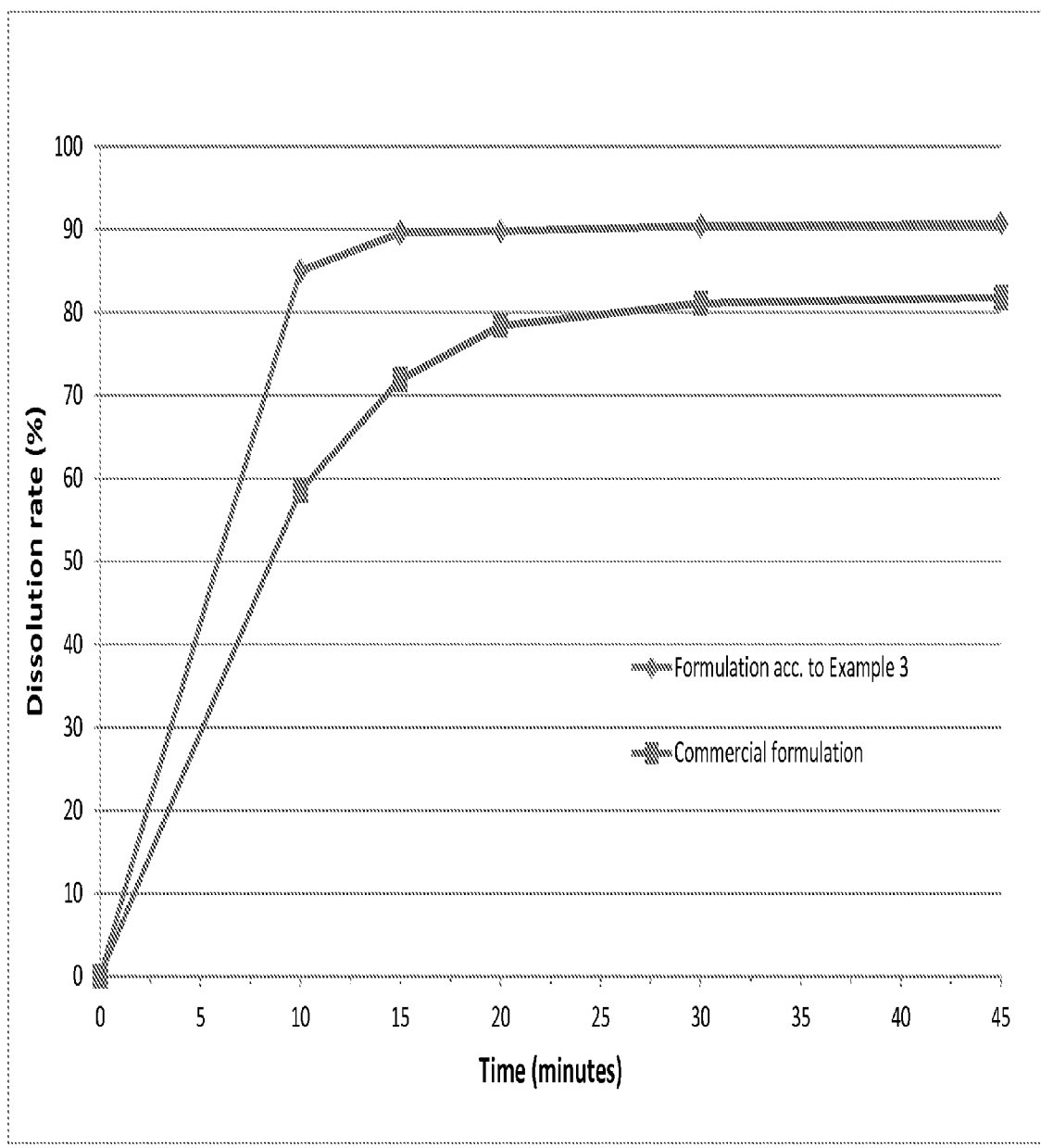
FIG. 3: Comparative dissolution profiles of tablet formulations containing 5 mg pimobendan prepared according to Example 3 of the invention and available commercially as chewing tablets, respectively in neutral acidic pH region (pH 7.5). Conditions of testing are the same as for FIG. 1.

The absorption of pimobendan highly depends on the dissolution rate of the active substance at varying pH conditions representing the gastrointestinal tract. The dissolution profiles of pimobendan from tablets prepared according to Example 3 of the present invention and commercially available chewable tablets, both containing 5 mg active substance were compared at different pH conditions representing the gastrointestinal tract. The results are presented in FIGS. 1 to 3. As can be seen from these data, the dissolution rate of pimobendan from the tablet formulation prepared according to the present invention was rapid and substantial at each pH tested. At pH 1.2 the speed and rate of dissolution from the formulation according to the present invention and the commercially available chewable tablets were practically the same. However, at pH 4.5 and 7.5, the dissolution of the active substance was faster and more extensive from the tablet formulation according to the invention than from the reference product. These results clearly demonstrate that the tablet formulation prepared according to the invention ensures a very satisfactory dissolution of pimobendan at all conditions representing the gastrointestinal tract, even if there are considerable pH fluctuations in it, without comprising any organic carboxylic acid which is present in great amounts in the commercially available product.

| | Dissolution rate (%) - pH 1.2 | | | | | |
|---|---|---|---|---|---|---|
| Time (min) | 0 | 10 | 15 | 20 | 30 | 45 |
| Formulation acc. to Example 3 | 0 | 86.8 | 91.0 | 92.7 | 94.1 | 96.2 |
| Commercial formulation | 0 | 74.9 | 90.0 | 93.7 | 93.8 | 94.5 |

| | Dissolution rate (%) - pH 4.5 | | | | | |
|---|---|---|---|---|---|---|
| Time (min) | 0 | 10 | 15 | 20 | 30 | 45 |
| Formulation acc. to Example 3 | 0 | 88.2 | 92.3 | 93.2 | 93.8 | 93.8 |
| Commercial formulation | 0 | 62.0 | 77.8 | 85.7 | 88.7 | 88.4 |

| | Dissolution rate (%) - pH 7.5 | | | | | |
|---|---|---|---|---|---|---|
| Time (min) | 0 | 10 | 15 | 20 | 30 | 45 |
| Formulation acc. to Example 3 | 0 | 85.0 | 89.6 | 89.8 | 90.4 | 90.7 |
| Commercial formulation | 0 | 58.6 | 71.9 | 78.4 | 81.1 | 81.8 |

Example 7—In Vitro Dissolution

The dissolution profiles of pimobendan and benazepril from tablets prepared according to Example 5 and containing 2.5 mg pimobendan and 5 mg benazepril were compared to commercially available chewable tablet formulations in pH 1.2, 4.5 and 7.5 buffers. The results obtained from the present study demonstrate that the dissolution of pimobendan and benazepril from the formulation containing both active substances in the lipid-embedded form is slower than from the corresponding commercial formulations containing only one active substance, i.e. either pimobendan or benazepril, the dissolution rate of both active compounds at 45 min of dissolution is higher from the combination than from the commercial mono formulations at each pH condition representing the gastrointestinal tract of dogs.

| | Dissolution rate (%) - pH 1.2 | | | | | | | | | | |
|---|---|---|---|---|---|---|---|---|---|---|---|
| Time (min) | 0 | 10 | | 15 | | 20 | | 30 | | 45 | |
| | | Pimo | Bena | Pimo | Bena | Pimo | Bena | Pimo | Bena | Pimo | Bena |
| Formulation according to Example 5 | 0 | 32 | 33 | 48 | 47 | 62 | 59 | 82 | 78 | 89 | 88 |
| Commercial Pimobendan formulation | 0 | 63 | — | 75 | — | 83 | — | 87 | — | 87 | — |
| Commercial Benazepril formulation | 0 | — | 56 | — | 71 | — | 76 | — | 80 | — | 84 |

Pimo = pimobendan;
Bena = benazepril

| | Dissolution rate (%) - pH 4.5 | | | | | | | | | | |
|---|---|---|---|---|---|---|---|---|---|---|---|
| Time (min) | 0 | 10 | | 15 | | 20 | | 30 | | 45 | |
| | | Pimo | Bena | Pimo | Bena | Pimo | Bena | Pimo | Bena | Pimo | Bena |
| Formulation according to Example 5 | 0 | 38 | 24 | 55 | 37 | 67 | 48 | 82 | 63 | 82 | 69 |
| Commercial Pimobendan formulation | 0 | 58 | — | 68 | — | 72 | — | 74 | — | 73 | — |
| Commercial Benazepril formulation | 0 | — | 34 | — | 45 | — | 53 | — | 58 | — | 63 |

Pimo = pimobendan;
Bena = benazepril

| Time (min) | 0 | | Dissolution rate (%) - pH 7.5 | | | | | | | |
|---|---|---|---|---|---|---|---|---|---|---|
| | | 10 | | 15 | | 20 | | 30 | | 45 |
| | Pimo | Pimo | Bena | Pimo | Bena | Pimo | Bena | Pimo | Bena | Pimo | Bena |
| Formulation according to Example 5 | 0 | 43 | 33 | 59 | 48 | 70 | 60 | 80 | 73 | 81 | 78 |
| Commercial Pimobendan formulation | 0 | 51 | — | 60 | — | 64 | — | 67 | — | 67 | — |
| Commercial Benazepril formulation | 0 | — | 54 | — | 61 | — | 63 | — | 62 | — | 60 |

Pimo = pimobendan;
Bena = benazepril

Example 8—Palatability (Acceptance) Test 30 male and female dogs of different breeds and age were tested at a shelter environment. The testing person offered to each dog a single daily dose of the tablet formulation prepared according to Example 3 of the invention which was adapted to the body weight of the animal for 3 days. In the case of tablet formulations of the present invention, in a first instance the tablet was offered by hand for 30 seconds. If the dog did not take the formulation it was offered the dog in his empty bowl. The dog had again 30 seconds to take the formulation. If one of the abovementioned offers lead to the dog willingly eaten the tablet, this was evaluated as acceptance or voluntarily uptake of the tablet. If the dog spit out the tablet it was reported as not accepted. A voluntarily uptake was observed in 82 out of the 90 possible opportunities (i.e. when offered to 30 animals for 3 days). This compares to an acceptance rate of 91.1%.

REFERENCES

1. EP 0 008 391
2. EP 0 439 030
3. EP 2 338 493
4. WO 2005/084647
5. WO 2010/010257
6. WO 2010/055119

What is claimed is:

1. A method for the preparation of a composition, the process comprising:
   dispersing particulate pimobendan in a molten carrier matrix to form particles coated with the carrier matrix, wherein the molten carrier matrix comprises one or more pharmaceutically acceptable carriers selected from the group consisting of a polyglycolized glyceride, a polyethylene glycol, and combinations thereof;
   atomizing the dispersion of coated particles; and
   cooling and collecting the coated particles from the atomized dispersion.

2. The method of claim 1, wherein the particulate pimobendan has a mean particle size of less than 20 μm, the carrier matrix has a melting point from 40° C. to 80° C., and the dispersing is performed in a high shear mixer to obtain a homogenous suspension of the coated particles within the carrier matrix.

3. The method of claim 1, wherein the carrier matrix comprises a polyglycolized glyceride.

4. The method of claim 1, wherein the polyglycolized glyceride comprises a stearoyl macrogol-32 glyceride, a lauroyl macrogolglyceride or a stearoyl macrogolglyceride.

5. The method of claim 1, wherein the polyethylene glycol has an average molecular weight of 1,500 to 20,000 g/mol, or an average molecular weight of 4,000 to 6,000 g/mol.

6. The method of claim 1, wherein the polyethylene glycol comprises PEG 6000.

7. The method of claim 1, wherein the atomizing the dispersion of coated particles is performed using an atomizer selected from the group consisting of a rotary atomizer, a pressure or pneumatic nozzle, a sonic nozzle, and combinations thereof.

8. The method of claim 1, wherein the atomizing the dispersion of coated particles is performed using a two-fluid pressure or pneumatic nozzle atomization system fitted in a spray congealing/chilling apparatus and using atomizing gas pressures of 1 to 10 bar.

9. The method of claim 1, wherein the cooling and collecting the coated particles from the atomized dispersion comprises applying a stream of cool air or an inert gas at a temperature of 0° to 30° C. from a spray apparatus to the coated particles within a cyclone separator or a bag filter.

10. The method of claim 9, wherein the cool air or inert gas is applied at a temperature of 5° to 15° C., or at a temperature of 4° to 8° C.

11. The method of claim 1, further comprising:
   blending the cooled and collected coated particles with one or more additional components to form a blended mixture; and
   compressing the blended mixture to form a tablet.

12. The method of claim 11, wherein the one or more additional components comprises one or more additional active ingredients.

* * * * *